US005250067A

United States Patent [19]

Gelfer et al.

[11] Patent Number: 5,250,067

[45] Date of Patent: Oct. 5, 1993

[54] BODY TREATMENT PAD HAVING A MULTIPLE NUMBER OF SHARPENED SKIN-PENTRATION PROTUBERANCES

[76] Inventors: Ala Gelfer; Arkadiy Gelfer, both of 600 S. Curson #326, Los Angeles, Calif. 90036; Stan Gelfer, 1022 N. Vista St. #5, Los Angeles, Calif. 90046

[21] Appl. No.: 984,228

[22] Filed: Nov. 30, 1992

[51] Int. Cl.$^5$ .............................................. A61B 17/34

[52] U.S. Cl. .................................... 606/189; 606/185; 606/186; 606/204; 606/201

[58] Field of Search ................ 128/907; 606/185, 186, 606/189, 201, 204

[56] References Cited

U.S. PATENT DOCUMENTS

| | | | |
|---|---|---|---|
| 3,987,787 | 10/1976 | Boxer | 606/204 |
| 4,411,258 | 10/1983 | Pujals, Jr. | 606/204 |
| 5,158,073 | 10/1992 | Bukowski | 606/204 |

FOREIGN PATENT DOCUMENTS

| | | | |
|---|---|---|---|
| 3404528 | 2/1984 | Fed. Rep. of Germany | 606/204 |
| 1667864 | 8/1991 | U.S.S.R. | 606/189 |

*Primary Examiner*—C. Fred Rosenbaum
*Assistant Examiner*—Noelle Kent Gring
*Attorney, Agent, or Firm*—Erik M. Arnhem

[57] ABSTRACT

An acupuncture treatment pad includes a flexible backing sheet having a multiplicity of similarly constructed rigid blocks at spaced points along the sheet surface. Each block has at least one tapered protuberance extending away from the sheet surface to form a relatively sharp edge or point; each protuberance can be a conical needle element, or alternately, a triangular cross-section knife element. When the pad is held under pressure against a person's body the sharpened protuberances act as acupuncture elements to stimulate nerve endings under the skin, thereby increasing the blood circulation and relieving pain experienced in damaged tissue deprived of adequate blood flow.

18 Claims, 1 Drawing Sheet

BODY TREATMENT PAD HAVING A MULTIPLE NUMBER OF SHARPENED SKIN-PENTRATION PROTUBERANCES

BACKGROUND OF THE INVENTION

1. Field of the Invention

The invention relates to an acupuncture treatment device comprising a flexible pad adapted to be pressed against a person's skin to stimulate blood circulation and safely relieve pain caused by stress, exercise or accident.

2. Prior Developments

The invention concerns a flexible pad having a large multiplicity of rigid needle-like protuberances or sharpened knife-like protuberances adapted to penetrate or depress a person's skin when the pad is pressed against the person's body. The sharpened protuberances act as acupuncture points to stimulate nerve endings under the skin so as to increase blood circulation and thereby ease or relieve pain experienced by the person being treated with the flexible pad.

I am aware of some prior art patents relating to flexible pad constructions designed to massage or treat the human body. U.S. Pat. No. 4,411,258 issued to C. Piyals on Oct. 25, 1983, discloses a flexible pad that may be held against a person's back by means of a flexible belt that is adapted to be wrapped around the person's torso. The flexible pad has several cone-shaped projections adapted to engage the person's skin so as to stimulate the skin tissues. Each cone-shaped projection has a tip area that is deflectable so as to avoid any piercing action of the person's skin. The projections are widely spaced, with a preferred spacing being approximately one and three eighth inch.

The patent to Altmeyer dated Aug. 13, 1963, U.S. Pat. No. 3,100,483, discloses a foot exerciser pad formed of soft rubber and having a series of different height projections distributed along the pad surface; the projections have rounded upper ends. The person stands on the pad and shifts his/her feet along the rounded projections so that the upper ends of the projections engage the arch portions of each foot, thereby exercising the foot muscles and stimulating the blood circulation.

U.S. Pat. No. 1,554,510, issued to E. W. Kirby on Sep. 22, 1925, shows a device for applying creams and pastes to a person's face while at the same time massaging the skin surface so as to exert a cleansing or softening effect. The device comprises a flat plate formed of soft pliable rubber, and having a large multiplicity of projections spaced therealong; each projection has a rounded end surface. A shroud wall is attached to an end portion of the flat plate to form a mitten-like insertion space for the person's fingers, whereby the person can manipulate the pliable plate along the skin surface to spread pastes and creams, and/or to massage the paste into the skin.

U.S. Pat. No. 1,741,962 issued to A. Theodoropulos, shows a massaging block carried on an elongated belt or strap; the massage block has a recess therein for a quantity of soap. The block and belt surface are each formed with projections, whereby a person can grasp the ends of the belt to rub the projections against the skin surface. Openings are formed in the block for enabling soap to flow onto the massaged areas of the skin, such that dirt particles are loosened and emulsified during the skin massaging action. The ends of the projections are blunt, presumably to prevent any penetration of the projections into the skin surface.

Russian patent SU 1489773-A1 discloses a massage device in the form of an elongated massage element adapted to extend transversely along the knuckles of a person's hand; a slot-like opening is formed in the massage element such that the person can insert his/her fingers through the opening to grip the massage element. A frontal surface of the massage element has a series of pointed projections extending therealong so that apparently the projections can be pressed against the skin area of a person being treated during a massaging operation.

SUMMARY OF THE INVENTION

This invention relates to an acupuncture treatment pad that comprises a flexible sheet having a plurality of similarly-constructed rigid blocks affixed to one face of the sheet at spaced points therealong. Each rigid block has one or more sharp edged protuberances extending away from the sheet so that when the pad is pressed against a person's skin the sharp edges penetrate or depress the skin to exert an acupuncture effect. The protuberances may be conical in nature, in which case the sharp edges will be defined by the sharpened pointed ends of the conical elements. Alternately, the protuberances may comprise elongated linear bars having triangular cross sections; in such case the sharp edges will comprise elongated knife-like edges formed by convergent side surfaces of the bars.

Each rigid block is independently affixed to the associated flexible backing sheet so that the various blocks can conform to a person's body contour, e.g. the person's arm or wrist, or a person's forehead, or a person's back or shoulder area. In use of the pad, the pad is pressed against the skin surface where the person is experiencing pain or discomfort. For example a person can lie in a prone position and hold the pad against his/her forehead while applying hand pressure to the pad exterior surface; the sharp edged protuberances will thereby be forced into the skin surface to stimulate nerve endings under the skin, thus increasing blood circulation and easing the pain. The flexibility of the backing sheet and the manner of mounting the blocks on the sheet enable the pad to conform to any part of the body experiencing. For example, the flexible pad can be wrapped around a person's arm or leg, such that the sharpened edges (ends) of the various protuberances can penetrate different circumferential portions of the limb (arm or leg). The action of the sharpened protuberances is in the nature of a mild acupuncture treatment. Usually the treatment period will be no longer than a few minutes. The flexible pad is not designed to be worn or applied to the person's body for prolonged lengths of time.

THE DRAWINGS

DESCRIPTION OF A PREFERRED EMBODIMENT OF THE INVENTION

FIGS. 1 through 4 illustrate an acupuncture treatment pad that includes a flexible backing sheet 10 and a plurality of similarly constructed rigid blocks 11 affixed to one face of the backing sheet. Sheet 10 can be canvas, or heavy cloth, or a thin sheet of non-woven plastic material; a prime consideration is that the sheet have sufficient flexibility to conform to the contours of a person's body, e.g. wrapped around a person's arm, or lying against a person's back.

Figure 1:
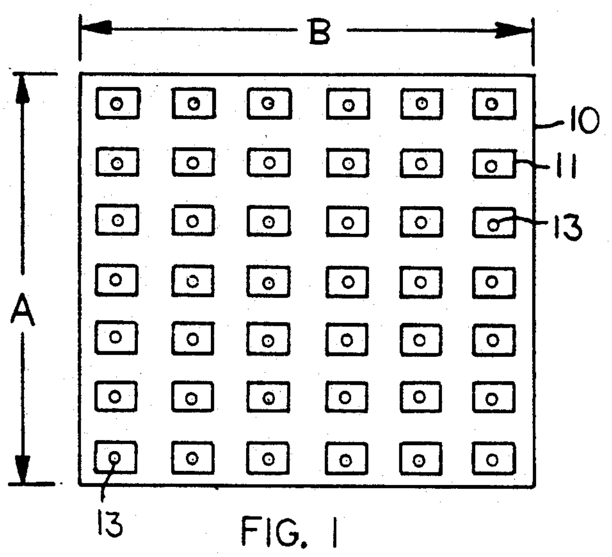
FIG. 1 is a plan view of an acupuncture treatment pad constructed according to the invention.

Sheet 10 can be of various dimensions. However, typically the sheet will have a dimension A measuring about ten inches, and a dimension B measuring about eleven inches. Each rigid block 11 can have a length dimension of about one inch and a width dimension of about 0.6, as viewed in FIG. 1. Each block is formed of a rigid hard plastic material, such that the block will not flex or deform under normal usage, i.e. when pressed against a person's body. The various blocks are spaced apart along the length and width dimensions of backing sheet 10, such that the various blocks will stay clear of one another when the flexible sheet is trained around the arm or leg of a person being treated. The flexible pad is applied to the person's body so that the various blocks 11 are engaged with the person's skin; i.e. sheet 10 is spaced from the person's skin (by the thickness of the blocks). The block spacing can be slightly less than the corresponding block dimension, as shown in FIG. 1. Each block 11 can be glued to the surface of sheet 10. However, each block is preferably affixed to the sheet by means of a single rivet 13 extending through the block at the geometrical center of the block. Use of a single rivet is advantageous in that the block can slightly swivel or pivot relative to the sheet, thereby the block to seat flatwise against the skin surface irrespective of the angulation of sheet 10.

Figure 3:
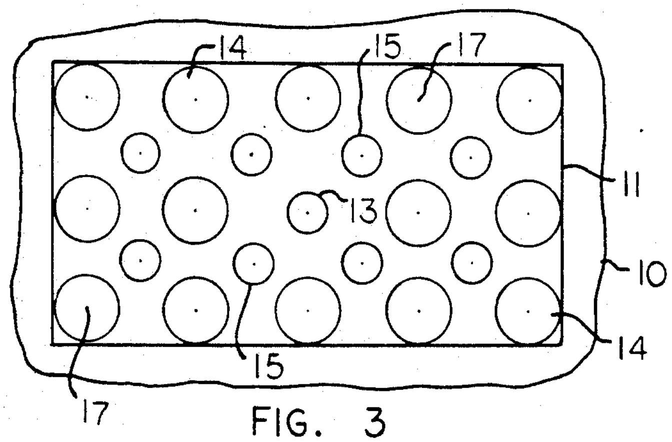
FIG. 3 is an enlarged plan view of a block structure used in the FIG. 1 acupuncture pad.
Figure 4:
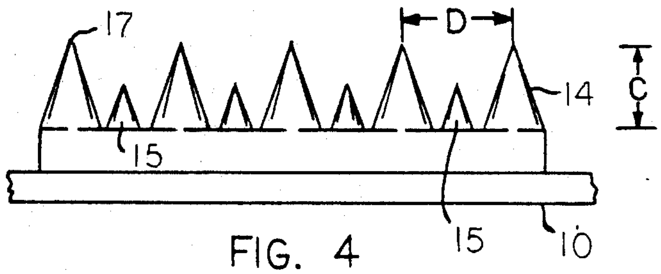
FIG. 4 is an edge view of the FIG. 3 block structure.

As shown in FIGS. 3 and 4, a representative block 11 has a multiplicity of closely spaced conical protuberances extending away from backing sheet 10. The protuberances comprise three rows of relatively long rigid protuberances 14, and a series of relatively short rigid protuberances 15 interspersed between the long protuberances 14. The long protuberances 14 are arranged in a square pattern, such the protuberance 14 spacing in each row is the same as the spacing between the rows. Each relatively short protuberance 15 is located on two imaginery diagonal lines connecting diagonally related long protuberances 14 in adjacent rows, whereby each short protuberance 15 is located equidistant from four of the long protuberances 14.

The protuberances may have various lengths while still practicing the invention. However, in a preferred arrangement each long protuberance 14 has a length dimension C of approximately five thirty secondth inch, whereas each short protuberance 15 has a corresponding length dimension of approximately three thirty secondth inch. The difference in the length dimensions of the long and short protuberances is then approximately one sixteenth inch. Each protuberance 14 or 15 has a cone angle of approximately forty degrees.

The various protuberances are spaced relatively close together so as to provide a relatively large number of protuberances in a relatively small size block. The spacing of the long protuberances, as indicated by dimension D in FIG. 4, is preferably about three sixteenth inch. In the illustrated block structure each block has fourteen long protuberances 14 and eight short protuberances 15.

When the acupuncture pad is placed in effective pressure contact with a person's body, the various conical protuberances 14 and 15 in each block have the pointed (sharpened) ends 17 thereof in pressure contact with the skin surface. Each long protuberance 14 will extend slightly further into the skin surface than the associated short protuberance 15. With a reasonably large application of pressure on the pad, the various protuberances 14 will depress the skin surface at the tip ends 17 of the protuberances, without breaking the skin surface, i.e., without producing a flow of blood. The relatively long protuberances 14 serve as acupuncture needle elements. The relatively short protuberances 15 serve as acupuncture needle elements, and also as reinforcement elements to prevent excessive penetration of the long protuberances 14 into the skin surface. The various protuberances 14 and 15 in each block share the pressure loading produced by the application of pressure on the pad.

The general effect of the acupuncture pad on the person's body is to stimulate nerve endings under the skin, so as to increase blood circulation and ease paid in the area being treated. The acupuncture pad can be used on any part of the body, e.g. the forehead, neck, shoulders, arms, back, legs, or feet. The treatment time is relatively short, on the order of one to three minutes.

The method of applying pressure to the flexible pad will vary, depending on the part of the body being treated. In some cases the pad can be positioned on a flat or curved support surface, so that the person can lie on the upwardly facing block projections 14 and 15. In some situations the person can stand on the blocks so that the block projections penetrate the soles of the person's feet. The pad can also be wrapped partially around a person's arm or leg, while the person applies hand pressure to the backing sheet 10. The extent of penetration of conical protuberances 14 and 15 into the person's skin can be adjusted by simply varying the hand pressure or weight distribution on sheet 10.

Figure 5:
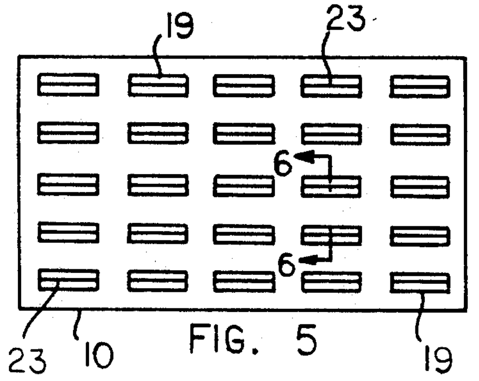
FIG. 5 is a plan view of a second acupuncture pad embodying the invention.
Figure 2:
FIG. 2 is an edge view of the FIG. 1 pad looking in the direction of arrow 2 in FIG. 1.
Figure 6:
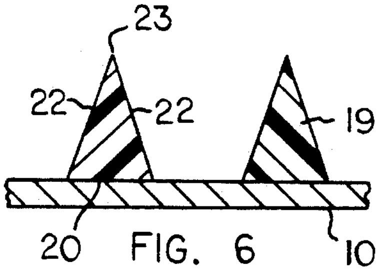
FIG. 6 is an enlarged fragmentary sectional view taken on line 6—6 in FIG. 5.

FIGS. 5 and 6 show a second form of the invention wherein each acupuncture block comprises an elongated bar 19 having a triangular cross section, as viewed in FIG. 6. Flat side surface 20 of the bar is adhesively attached to a flexible backing sheet 10, whereas convergent side surfaces 22 extend away from the sheet to form an elongated knife edge 23. The defined knife edge 23 may have an included angle of about forty degrees or less.

As viewed in FIG. 5, each bar 19 has a length dimension that is approximately three times its transverse width dimension. Typically the length of each bar 19 can be about one and one half inch or less. The height dimension of each triangular cross-sectioned bar 19 can be about one fourth inch.

The acupuncture pad of FIGS. 5 and 6 will be used in essentially the same fashion as the pad of FIGS. 1 through 4. When the pad is pressured against a person's body, knife edges 23 penetrate the skin surface to stimulate nerve endings under the skin, thereby increasing the blood circulation and easing the painful condition associated with damaged tissue deprived of adequate blood flow.

In both forms of the invention the flexible pad is held against the person's body in a relatively stationary condition. The pad is not moved along the skin surface. Pain relief is achieved by an acupuncture action produced by the tapered protuberances, i.e. the conical protuberances of FIG. 4 or the triangular knife edge protuberances of FIG. 6. While the term "penetration" has been used herein to describe the action of the tapered protuberances on the skin surface, it should be realized that this term is not meant to imply a rupture or cutting of the skin surface; instead the term is intended to mean a depressing action on the skin, such that the skin is indented measurably at the points where the conical tip or knife edge digs into the skin surface.

With either form of the invention of the flexible pad can be rolled up into a spirally wound configuration for compact storage. The pad is put into use merely by unwinding the pad to a flat condition and applying the pad to the afflicted area of the body.

The invention has been illustrated and described in two specific embodiments. However, it will be appreciated that the invention can be practiced in various forms and configurations.

What is claimed is:

1. An acupuncture treatment pad comprising a flexible backing sheet; a plurality of similarly-constructed rigid blocks affixed to one face of said sheet at evenly spaced points therealong; each block having a large multiplicity of closely spaced conical protuberances extending away from said flexible sheet; said protuberances comprising a first set of relatively long rigid protuberances, and a second set of relatively short rigid protuberances; said relatively long protuberances being arranged in a square pattern that comprises a plurality of evenly spaced rows, the protuberance spacing in each row being the same as the spacing between rows; each relatively short protuberance being located equidistant from four of the relatively long protuberances on two imaginary diagonal lines connecting diagonally related protuberances in adjacent rows; each rigid block being independently affixed to said flexible sheet so that the blocks can conform to a person's body contours, with each of the relatively long protuberances in a given block being engaged with the person's skin.

2. An acupuncture treatment pad according to claim 1, wherein each relatively long protuberance has a cone angle of approximately forty degrees.

3. An acupuncture treatment pad according to claim 2, wherein each long protuberance has a height that is approximately one sixteenth inch greater than the height of each short protuberance.

4. An acupuncture treatment pad according to claim 1, wherein there are at least three rows of long protuberances on each rigid block, each row having at least four long protuberances therein.

5. An acupuncture treatment pad according to claim 1, wherein the long protuberances on each rigid block have cone centerlines that are spaced apart approximately three sixteenth inch.

6. An acupuncture treatment pad according to claim 1, wherein the block spacing is approximately the same as the corresponding block lateral dimension.

7. An acupuncture treatment pad comprising a flexible backing sheet; a plurality of similarly-constructed rigid blocks affixed to one face of said sheet at spaced points therealong; each block having a multiplicity of rigid conical protuberances extending away from said flexible sheet; said protuberances comprising a first set of relatively long protuberances, and a second set of relatively short protuberances; said relatively long protuberances being evenly spaced apart; said relatively short protuberances being arranged between selected long protuberances in an evenly spaced relationship; each rigid block being independently affixed to said flexible sheet so that the blocks can conform to a person's body contours, with each of the relatively long protuberances in a given block being engaged with the person's skin.

8. An acupuncture treatment pad according to claim 7, wherein each relatively long protuberance has a cone angle of approximately forty degrees.

9. An acupuncture treatment pad according to claim 8, wherein each long protuberance has a height that is approximately one sixteenth inch greater than the height of each short protuberance.

10. An acupuncture treatment pad according to claim 9, wherein the long protuberances on each rigid block have cone centerlines, that are spaced apart approximately three sixteenth inch.

11. An acupuncture treatment pad according to claim 10, wherein the block spacing is approximately the same as the corresponding block lateral dimension.

12. An acupuncture treatment pad comprising a flexible backing sheet; a plurality of similarly-constructed rigid blocks affixed to one face of said sheet at spaced points therealong; each block having at least one tapered protuberance extending away from said flexible sheet; each tapered protuberance having a sharpened end adapted to penetrate a person's skin when the massage pad is in pressure engagement with a person's body; each rigid block being independently affixed to said flexible sheet so that the blocks can conform to a person's body contours.

13. An acupuncture treatment pad according to claim 12, wherein each rigid block comprises an elongated bar having a flat side surface affixed to said flexible sheet, and two upstanding convergent side surfaces cooperatively defining an elongated knife-like end edge.

14. An acupuncture treatment pad according to claim 13, wherein each elongated knife-like end edge has an included angle of approximately forty degrees.

15. An acupuncture treatment pad according to claim 14, wherein each rigid block has a length dimension parallel to the knife-like end edge, and a width dimension transverse to the knife-like end edge; the length dimension of each block being several times the block width dimension.

16. An acupuncture treatment pad according to claim 12, wherein each rigid block has a multiplicity of rigid conical protuberances extending away from said flexible sheet.

17. An acupuncture treatment pad according to claim 16, wherein each protuberance has a cone angle of approximately forty degrees.

18. An acupuncture treatment pad according to claim 16, and further comprising a single rivet extending through each rigid block and the associated backing sheet, whereby each block is affixed to the sheet by a single rivet; each rivet being centrally located on the geometrical center of the associated block.

* * * * *